US007759355B2

(12) United States Patent
Kase et al.

(10) Patent No.: US 7,759,355 B2
(45) Date of Patent: Jul. 20, 2010

(54) ADENOSINE A2A RECEPTOR ANTAGONISTS FOR TREATING RESTLESS LEGS SYNDROME OR NOCTURNAL MYOCLONUS

(75) Inventors: Hiroshi Kase, Koganei (JP); Naoki Seno, Moriya (JP); Akihisa Mori, Narashino (JP); Dayao Zhao, Mystic, CT (US)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 624 days.

(21) Appl. No.: 10/523,603

(22) PCT Filed: Aug. 27, 2003

(86) PCT No.: PCT/US03/26644

§ 371 (c)(1), (2), (4) Date: Feb. 4, 2005

(87) PCT Pub. No.: WO2004/019949

PCT Pub. Date: Mar. 11, 2004

(65) Prior Publication Data
US 2005/0245545 A1 Nov. 3, 2005

Related U.S. Application Data

(60) Provisional application No. 60/406,955, filed on Aug. 30, 2002.

(51) Int. Cl.
A61K 31/522 (2006.01)
A61P 25/00 (2006.01)
A61P 25/14 (2006.01)

(52) U.S. Cl. .............................. 514/263.2; 514/263.34; 514/264.1; 514/267; 544/272; 544/273

(58) Field of Classification Search ................. 514/263, 514/264, 267, 263.34, 263.2, 264.1; 544/272, 544/273
See application file for complete search history.

(56) References Cited

U.S. PATENT DOCUMENTS

| 5,484,920 | A | 1/1996 | Suzuki et al. ............... 544/268 |
| 5,587,378 | A * | 12/1996 | Suzuki et al. ........... 514/263.24 |
| 6,346,283 | B1 | 2/2002 | Hoffman et al. |
| 6,544,565 | B2 | 4/2003 | Hoffman et al. |
| 2002/0064569 | A1 | 5/2002 | Hoffman et al. |
| 2004/0198753 | A1 | 10/2004 | Kase et al. |
| 2006/0148827 | A1 | 7/2006 | Kase et al. |
| 2006/0178379 | A1 | 8/2006 | Kase et al. |
| 2008/0176873 | A1 | 7/2008 | Streeper et al. |

FOREIGN PATENT DOCUMENTS

WO 00/57894 10/2000

WO 03/063876 8/2003

OTHER PUBLICATIONS

Trenkwalder, C. "Sleep dysfunction in Parkinson's disease", Clin Neurosci. 1998, 5(2), pp. 107-114.*
Evidente, "Amantadine Is Beneficial in Restless Legs Syndrome", Movement Disorders, vol. 15, No. 2, 2000, pp. 324-327.*
Tan, et al., "Restless legs syndrome in Parkinson's Disease", J. Neurol. Sci., vol. 196 (2002) 33-6.
Muller, et al., "Interactions of valerian extracts and a fixed valerian—hop extract combination with adenosine receptors", Life Sciences, vol. 71 (2002) 1939-49.
Radioligandbindungsstudien, Affinität verschiedener Baldrianextrakte zu A1-, A2A und A3-Adenosinrezeptoren, D3, 1-3.
Functional Studies, Adenosine-A2A-receptor-induced intracellular cAMP-accumulation und inhibition thereof, D4, 1-3.
Allen, et al., "Restless Legs Syndrome, A Review of Clinical and Pathophysiologic Features", Journal of Clinical Neurophysiology, vol. 18, No. 2 (2001) 128-47.
Richardson, et al., "Adenosine A2A receptor antagonists as new agents for the treatment of Parkinson's disease", TIPS, vol. 18 (1997) 338-44.
Shiozaki, et al., "Actions of adenosine A2A receptor antagonist KW-6002 on drug-induced catalepsy and hypokinesia caused by reserpine or MPTP", Psychopharmacology, vol. 147 (1999) 90-5.
Muller, "A2A adenosine receptor antagonists—future drugs for Parkinson's disease", Drugs of the Future, vol. 25, No. 10 (2000) 1043-52.
Evidente, et al., "Amantadine Is Beneficial in Restless Legs Syndrome", Movement Disorders, vol. 15, No. 2 (2000) 324-27.
Ondo, et al., "Exploring the Relationship Between Parkinson Disease and Restless Legs Syndrome", Arch. Neurol., vol. 59 (2002) 421-24.
Moreau, et al., "Central adenosine A2A receptors: an overview", Brain Research Reviews, vol. 31 (1999) 65-82.
Kase, "New Aspects of Physiological and Pathophysiological Functions of Adenosine A2A Receptor in Basal Ganglia", Biosci. Biotechnol. Biochem., vol. 65, No. 7 (2001) 1447-57.
Lutz, "Restless Legs, Anxiety and Caffeinism", J. Clin.Psychiatry, vol. 39 (1978) 693-98.
Muller, et al., "Synthesis of Paraxanthine Analogs (1,7-Disubstituted Xanthines) and Other Xanthines . . . ", J. Med. Chem., vol. 36 (1993) 3341-49.
Slawsky, et al., "Rolofylline: a selective adenosine 1 receptor antagonist for the treatment of heart failure", Expert Opin. Pharmacother., vol. 10, No. 2 (2009) 311-22.
Walther, "Treating restless legs syndrome: current pathophysiological concepts and clinical trials", Expert.Opin. Investig. Drugs, vol. 11, No. 4 (2002) 501-14.
Manconi, "On the pathway of an animal model for restless legs syndrome", Neurol. Sci., vol. 28 (2007) S53-60.

(Continued)

*Primary Examiner*—Sreeni Padmanabhan
*Assistant Examiner*—Sahar Javanmard
(74) *Attorney, Agent, or Firm*—Fitzpatrick, Cella, Harper & Scinto

(57) ABSTRACT

The present invention provides methods of treating restless legs syndrome or related disorders, comprising administering an effective amount of at least one adenosine $A_{2A}$ receptor antagonist to a patient in need thereof. More preferably the adenosine $A_{2A}$ receptor antagonist is a xanthine derivative or a pharmaceutically acceptable salt thereof.

4 Claims, No Drawings

OTHER PUBLICATIONS

Askenasy, "Approaching disturbed sleep in late Parkinson's Disease: first step toward a proposal for a revised UPDRS", Parkinsonism and Related Disorders, vol. 8 (2001) 123-31.

Curriculum Vitae and a list of publications of Prof. C.E. Muller (17 pages).

Report on Comparative study on biotechnology patent practices, Theme: Comparative study on "reach-through claims" (2001) 1-19.

Lavigne et al., "Restless Legs Syndrome and Sleep Bruxism: Prevalence and Association Among Canadians", Sleep, vol. 17, No. 8 (1994) 739-43.

de Mello, et al., "Treatment of periodic leg movements with a dopaminergic agonist in subjects with total spinal cord lesions", Spinal Cord, vol. 37, No. 9 (1999) 634-37.

Yokota, et al., "Sleep related periodic leg movements (noctural myoclonus) due to spinal card lesion", J. Neurol. Sci., vol. 104, No. 1 (1991) 13-8.

Wetter et al., "A randomized controlled study of pergolide in patients with restless legs syndrome", Neurology, vol. 52, No. 5 (1999) 944-50.

Tan et al., "Restless legs syndrome in Parkinson's disease", J. Neurol. Sci., vol. 196 (2002) 33-6.

Collado-Seidel et al., "Clinical and Biochemical Findings in Uremic Patients With and Without Restless Legs Syndrome", Am. J. Kidney Dis., vol. 31, No. 2 (1998) 324-8.

Godman, et al., "Restless leg syndrome in pregnancy", BMJ, vol. 297 (1988) 1101-1102.

Adams, et al., Principles of Neurology, 6th ed., 387.

Schmerz Rundsch Med. Prax., vol. 86, No. 18 (1997) 732-36.

Aoyama, et al., "Rescue of Locomotor Impairment in Dopamine D2 Receptor-Deficient Mice by an Adenosine A2A Receptor Antagonist", The Journal of Neuroscience, vol. 20, No. 15 (2000) 5848-52.

Schindler, et al., "Effects of dopamine agonists and antagonists on locomotor activity in male and female rats", Pharmacology Biochemistry and Behavior, vol. 72 (2002) 857-63.

"Myoclonus", www.merck.com/mmpe/print/sec16/ch221/ch221f.html.

* cited by examiner

ADENOSINE A2A RECEPTOR ANTAGONISTS FOR TREATING RESTLESS LEGS SYNDROME OR NOCTURNAL MYOCLONUS

FIELD OF THE INVENTION

The present invention relates to methods of treating restless legs syndrome or related disorders. The method of treatment is preferably by administering a pharmaceutical agent containing a therapeutically effective amount of an adenosine $A_{2A}$ receptor antagonist. More preferably the adenosine $A_{2A}$ receptor antagonist is a xanthine derivative. Most preferably, the adenosine $A_{2A}$ receptor antagonist is a xanthine derivative described in detail herein.

BACKGROUND OF THE INVENTION

Restless Legs Syndrome

Restless legs syndrome (RLS) is a distinctive but often misdiagnosed sensorimotor disorder. The general incidence of RLS is high and is the seventh most frequently diagnosed musculoskeletal disorder out of 103 diagnoses relating to these conditions [Arch. Intern. Med., 161, 483-484 (2001)]. RLS is also characterized as a sleep disorder and is frequently diagnosed as a cause of insomnia [Sleep Med., 2, 367-369 (2001); and Sleep, 23, 237-241 (2000)].

Although RLS was first described in the $17^{th}$ century, the classic features that define the syndrome were first presented in 1945 [The London practice of Physick. London: Bassett et al. Eds. (1962); and Acta Med. Scand. Suppl., 158, 1-123 (1945)]. Despite the number of years since RLS was first appreciated as a medical indication, diagnosis and treatment remain sub-optimal. Even though it may affect up to 10% of the US population, it is often unrecognized or misdiagnosed. In some cases, a cause can be found, such as iron-deficiency anemia, and the RLS can be cured. In general, however, motor restlessness is poorly diagnosed and treated [IJCP, 55, 320-322 (2001)].

Although the etiology of RLS is unknown, the primary anatomic localization of abnormal functioning in RLS is possibly in spinal system [Disord., 13(suppl 2), 294 (1998)]. Several new diagnostic tools may aid in identifying RLS [J. Neurol., 249, 164-170 (2002); and Clin. Neurophys., 113, 571-578 (2002)].

The features associated with RLS include dysesthesias deep in the limb that compel the person to move in order to relieve the sensation and that are engendered and exacerbated by rest, primarily in the evening and at night [HealthNews, Greene, Jun., 10 (2001)]. In 1995, the International RLS Study Group published the primary and associated features of this disorder [Mov. Dis., 10, 634-642 (1995)]. For recent reviews, see, Latorre & Irr (2001) http://www.emedicine.com/NEURO/topic509.htm; 2001 Medical Bulletin, Restless Legs Syndrome Foundation, Inc.; and Am. J. Med. Sci., 319, 397-403 (2000). Additional criteria of RLS include involuntary, rhythmic retraction movements occurring especially at night, and especially during sleep stages I and II; and sleep disturbance results in daytime fatigue.

Although RLS occurs as a component of several diseases, it is not indicative of these diseases [Sleep, 23, 361-367 (2000); Arch. Neurol., 59, 421-424 (2002); J. Neurol. Sci., 196, 33-36 (2002); and J. Neurol. Neurosurg. Psych., 72, 555 (2002)].

According to the Restless Legs Syndrome Foundation (www.rls.org), adults with RLS will typically have all four of the following primary features. First, the bothersome, but usually not painful, sensations deep in the legs produce an irresistible urge to move. Second, symptoms are worse or exclusively present when the afflicted individual is at rest, and the sensations are typically lessened by voluntary movement of the affected extremity. Third, symptoms are worse in the evening and at night, especially when the individual lies down. Fourth, movements of the toes, feet, or legs (known as restlessness) are typically seen when the afflicted individual is sitting or lying down in the evening. This restlessness may be seen as fidgetiness or nervousness.

The dysesthesias and accompanying urge to move occur most commonly during the evening or early part of the night (between 6 pm and 4 am) [Sleep, 22, 901-912 (1999); and Mov. Disord., 14, 102-110 (1999)]. Patients are less bothered by symptoms during the daytime and, even if severely affected, often obtain some relief near dawn. The symptoms progress over time in about two thirds of RLS patients and may be severe enough to be disabling, disrupting sleep and impacting on a patient's life and well-being.

Adults with RLS almost always describe these uncomfortable sensations or parenthesis, which most commonly occur in the legs, as being like an electric current, water moving, or insects crawling or as tingling, aching, or grabbing. A wide variety of other descriptions have been offered, and some patients cannot describe the sensations at all except as an urge to move the leg [Neurol., 47, 1435-1441 (1996)].

In a significant minority of individuals with RLS (perhaps 20% to 30%), similar sensations occur in the arms, usually in more severely affected patients later in the clinical course of their disorder [Eur. Neurol., 45, 67-74 (2001); and Eur. Neurol., 44, 133-138 (2000)]. Even less frequently, these sensations occur in the trunk or elsewhere. The sensations are not generally described as painful, but if asked directly, a minority (perhaps 20%) of patients will describe the sensations as painful.

The unpleasant limb sensations of RLS are precipitated by rest or inactivity such as lying in bed, riding in a car or airplane or sitting in a theater. Some patients describe increasing discomfort and involuntary limb jerking if they remain still. There is an urge to move the legs because relief is often gained after moving. To relieve the urge to move, patients typically walk around, although they may attempt to obtain relief through performing a wide variety of movements such as rocking, shaking, stretching, marching in place, pacing, or bending. Some patients obtain relief simply from standing.

These varied movements that patients select to reduce their symptoms are under voluntary control and can be suppressed on command. Suppression may greatly increase the patient's discomfort, however, and few severely affected individuals are capable of stifling their restless movements for more than a brief period when they are symptomatic. In rare cases, the movements may occur as the dominant symptoms with only very limited awareness of the urge to move.

In most cases, the cause of RLS is unknown. Such idiopathic disease can be familial and, if so, is transmitted in an autosomal dominant fashion. Progressive decrease in age at onset with subsequent generations has been described in some families. Patients with familial RLS tend to have an earlier age at onset and slower progression. Despite the use of dopaminergic agents to treat RLS, the genes involved in dopaminergic neurotransmission were found to have no influence on RLS [Neurol., 57, 1304-1306 (2001)].

Associated Features of RLS

RLS symptoms can cause difficulty in falling and staying asleep resulting in abnormal tiredness during waking hours. Chronic sleep deprivation and its resultant daytime sleepiness can affect the patient's ability to work, participate in social activities, and partake in recreational pastimes and can cause mood swings, which can affect their personal relationships.

RLS may be the result of another condition, which, when present, worsens the underlying RLS. This is called secondary RLS. During pregnancy, particularly during the last few months, up to 15% of women develop RLS. After delivery, their symptoms often vanish. Other causes include the following. Deficiency of iron, folate, B-12 or magnesium. Iron, folate and B-12 deficiencies can result in anemia. Magnesium deficiency is rare except in the presence of unusual diets. RLS can be the initial symptom of iron deficiency. Polyneuropathy can also lead to RLS. Polyneuropathy can be caused by alcohol abuse, amyloidosis, diabetes mellitus, lumbosacral radiculopathy, Lyme disease, rheumatoid arthritis, uremia or vitamin B-12 deficiency. Gastric surgery, which can lead to mal-absorption of foods. Chronic obstructive pulmonary disease (COPD) which can lead to changes in blood chemistry such as acidosis or alkalosis, low oxygen saturation, or retention of carbon dioxide. These changes in the blood chemistry can, in turn, irritate the peripheral nerves and result in RLS. Chronic venous insufficiency or varicose veins. Intake of certain drugs such as alcohol, caffeine, anticonvulsants, antidepressants, beta blockers, lithium or certain major tranquilizing agents. Abrupt withdrawal from certain drugs such as vasodilators, sedatives or antidepressants. Myelopathy or myelitis. Hypothyroidism or hyperthyroidism. Hypoparathyroidism or hyperparathyroidism. Acute intermittent porphrya. Liver failure. Cancer.

Though RLS is diagnosed most often in people in their middle years, many individuals with RLS, particularly those with primary RLS, can trace their symptoms back to childhood. These symptoms may have been called growing pains or the children may have been thought to be hyperactive because they had difficulty sitting quietly.

No laboratory test exists that can confirm a diagnosis of RLS. However, a thorough physical examination, including the results of necessary laboratory tests, can reveal temporary disorders, such as iron deficiency, that may be associated with RLS. Some patients will require an overnight testing of sleep to determine other causes of their sleep disturbance.

Treatment

If an underlying iron or vitamin deficiency is found to be the cause of a patient's restless legs, supplementing with iron, vitamin B12, or folate (as indicated) may be sufficient to relieve the symptoms. Current recommendations include checking a serum ferritin level (to evaluate iron-storage status) and supplementing with iron if the ferritin level is less than 50 μg/L. Patients with varicose veins have been found to benefit from use of sclerosing agents. Those with uremia may have relief after kidney transplantation or correction of anemia with erythropoietin.

The use of some medications seems to worsen the symptoms of RLS. These drugs include calcium-channel blockers, most antinausea medications, some cold and allergy medications, major tranquilizers, phenytoin, and most antidepressants.

Unfortunately, in many cases, the symptoms of RLS either initially do not resolve with the treatment of underlying disorders and the implementation of lifestyle changes or, over time, progress so that relief is insufficient with these methods. In either case, the use of medications may become necessary.

No drugs have been approved by the U.S. Food and Drug Administration for the treatment of RLS, but several drugs have undergone clinical studies in RLS and have been approved for other conditions. These medications fall into four main classes-dopaminergic agents, sedatives, pain relievers, and anticonvulsants. Each drug or class of drugs has its own benefits, limitations, and side-effect profile. The choice of medication is dependent upon the timing and severity of symptoms. Generally, treatment begins with a low dose taken an hour or two before bedtime. If tolerance to one drug develops, another class of drugs may be substituted.

Dopaminergic Agents

The primary and first-line treatment for RLS is with a dopaminergic agent [Expert Opin. Investig. Drugs, 11, 501-514 (2002); Neurol., 58(Suppl. 1), S87-S92 (2002); and Danek et al. In Neurological Disorders: Course and Treatment Academic Press, pp. 819-823 (1996)]. Involvement of altered activity of dopaminergic diencephalic spinal neurons that originate in A11 region [Brain Res., 342, 340-351 (1985)].

Although dopaminergic agents are used to treat Parkinson's disease, RLS is not a form of Parkinson's disease [J. Neurol. Sci., 196, 33-36 (2002)]. All of these drugs should be started at low doses and increased very slowly to decrease potential side effects. Due to the disabling side effects associated with long-term dopaminergic activation, chronic use of this class of drugs in RLS has not been adopted.

A variety of dopaminergic agents have been described for treating RLS. These include carbidopa, levodopa, carbidopa with levodopa (Sinemet), ropinerole, pramipexole, cabergoline, entacapone and, Piribedil [Mov. Dis., 17, 421 (2002); Mov. Dis., 16, 579-581 (2001); Eur. Neurol., 46(suppl 1), 24-26 (2001); U.S. Pat. Nos. 6,194,445; 6,114,326; 6,001,861; 5,945,424; and U.S. patent application No. 2001/0029262].

Dopaminergic agents can cause the side effect known as augmentation or rebound. Augmentation comprises an earlier onset of symptoms in the evening than before treatment, appearance of symptoms during the day, involvement of other body parts and an increased severity of symptoms. The only recourse is to stop taking the drug. Other side effects include nausea, dizziness, somnolence, insomnia, constipation, postural hypotension, asthenia and hallucination.

Sedatives

Sedative agents are most effective for relieving the nighttime symptoms of RLS. They are used either at bedtime in addition to a dopaminergic agent or for individuals who have primarily nighttime symptoms. The most commonly used sedative is clonazepam (Klonopin). Other suggested medications such as anti-histamines and NK1-receptor antagonists may function via their sedative effect.

Pain Relievers

Pain-relieving drugs are used most often for people with severe relentless symptoms of RLS. Some examples of medications in this category include codeine, Darvon or Darvocet (propoxyphene); Dolophine (methadone); Percocet (oxycodone); Ultram (tramadol); and Vicodin (hydrocodone). Opioids have been found to be the most effective at relieving symptoms, and relief has been found with intrathecal delivery of morphine or bupivacaine [Acta Anaesthesiol. Scand., 46, 114-117 (2002)]. Opioids are potent suppressors of RLS and PLMS, but the risks of abuse and addiction limit their use. Side effects and adverse reactions include dizziness, sedation, nausea, vomiting, constipation, hallucination and headache.

Anticonvulsants

These drugs are particularly effective for some, but not all, patients with marked daytime symptoms, particularly people who have pain syndromes associated with their RLS. Gabapentin (Neurontin) is the anticonvulsant that has shown the most promise in treating the symptoms of RLS [Neurol., 57, 1717-1719 (2001)].

Other Therapies

Other suggested treatments include transcutaneous electrical nerve stimulation, conditioning therapy, and various procedures to reduce incompetent veins, but none of these ancillary treatments has been clearly established to be effective [Health Technol. Assess., 1, 1-135 (1997); Sleep, 19, 442-444 (1996); and Dermatol. Surg., 21, 328-332 (1995)].

In particular, the Edinburgh vein study found that most lower-limb symptoms (including RLS) probably have a non-venous cause and surgical intervention (i.e., sclerotherapy or "vein stripping") is unlikely to alleviate the symptoms [Brit. Med. J., 318, 353-35 (1999)]. One group advocates medical therapy for what they call "hypotonic phlebopathy" (a mild form of venous insufficiency), but their clinical description coincides with the symptoms of RLS almost perfectly [Minerva Cardioangiol., 48, 277-285 (2000)].

Additional pharmaceutical agents have been proposed to treat RLS. These include 5HT antagonists; $\alpha_2$ antagonists such as Mirtazapine; NK1-receptor antagonists; anti-histamines; and an herbal extract of Valeriana [Neurol., 53, 1154 (1999); U.S. Pat. Nos. 6,346,283; 6,329,401; 6,319,927; 6,281,207; 6,214,837; and U.S. patent application Nos. 2002/0035057; 2001/0034320; 2002/0010201]. Mirtazapine, however, may cause RLS [Psych. Clin. Neurosci., 56, 209-210 (2002)].

Children

Recent literature also points toward an association between RLS and symptoms of attention-deficit hyperactivity disorder [Sleep, 25, 213-218 (2002)]. A few case reports and one case series have assessed treatment specific to children. These case reports have indicated individual responses to strict limit-setting in enforcing the child's sleep schedule, restricting caffeine consumption, and using medications such as clonazepam, carbidopa/levodopa, pergolide, or clonidine [Picchietti In Wilson, ed. Sleep thief: restless legs syndrome. Orange Park, Fla.: Galaxy Books pp. 82-94 (1996); Pediatr. Neurol., 22, 182-186 (2000); Sleep Res., 22, 70 (1993); Pediatr Neurol., 11, 241-245 (1994); and Sleep, 22, 297-300 (1999)].

Benzodiazepines, anticonvulsants, alpha-adrenergic agents, and opioids have been extensively used in children with disorders other than RLS, as has chronic use of levodopa for dopa-responsive dystonia [J. Am. Acad. Child Adolesc. Psych., 33, 424-426 (1994); and Neurol., 41, 174-181 (1991)]. An open-label trial of pergolide in the treatment of RLS in five children with RLS found that not only the sleep parameters, but also the children's scores of attention and impulsivity, improved [Pediatr. Neurol., 22, 182-186 (2000)].

PLMS

About 80% of patients with RLS have unilateral or bilateral periodic limb movements of sleep (PLMS), also called nocturnal myoclonus. Patients without RLS also experience PLMS. These movements are stereotyped, repetitive, slow flexion of the limbs (legs alone or legs more than arms) during the early stages of sleep. The movements occur semirhythmically at intervals of 5 to 60 seconds and last about 1.5 to 2.5 seconds. In the lower limbs, repetitive dorsi flexion of the big toe with fanning of the small toes is seen, along with flexion of the ankles, knees and thighs. Arm movements usually consist of the flexion of the forearm in combination with the wrist. There can be night-to-night variability in the number of movements.

PLMS can occur while patients are awake and are called dyskinesias. Such dyskinesias are uncommon but can occur in up to 50% or RLS patients.

PLMS increases with age. Thirty five percent or more of people aged 65 and older experience PLMS. PLMS also occurs in younger people, though less commonly. Men and women are equally affected. The exact cause of PLMS is still unknown. The underlying mechanisms probably involve factors in the nervous system, although studies have not revealed any consistent abnormalities.

PLMS are not considered medically serious. They can, however, be implicated as a contributing factor in chronic insomnia and/or daytime fatigue because they may cause awakenings during the night. Occasionally, PLMS may be an indicator of a serious medical condition such as kidney disease, diabetes or anemia.

A number of medications have been shown to be effective in treating PLMS, but treatment is only necessary when PLMS are accompanied by restless legs (RLS), insomnia or daytime fatigue.

Adenosine $A_{2A}$ Receptors

Adenosine is known to act via four major receptor subtypes, $A_1$, $A_{2A}$, $A_{2B}$, $A_3$, which have been characterized according to their primary sequences [Pharmacol. Rev., 46, 143-156 (1994)]. Adenosine $A_{2A}$ receptors are abundant in the caudate-putamen, nucleus accumbens, and olfactory tubercle in several species [Brain Res., 519, 333-337 (1990)]. A variety of $A_{2A}$ receptor antagonists have been synthesized (U.S. Pat. Nos. 6,262,106; 6,222,035; 6,197,788; 5,756,735; 5,703,085; 5,670,498; 5,565,460; and 5,484,920).

In the caudate-putamen, adenosine $A_{2A}$ receptors are localized on several neurons and have been shown to modulate the neurotransmission of γ-aminobutyric acid (GABA), acetylcholine and glutamate [J. Neurochem., 66, 1882-1888 (1996); J. Neurosci., 16, 605-611 (1996); Neuroscience, 100, 53-62 (2000); Trends Pharmacol. Sci., 18, 338-344 (1997); and Biosci. Biotechnol. Biochem., 65, 1447-1457 (2001)]. These actions of the $A_{2A}$ receptor contribute to the control of motor behavior since $A_{2A}$ receptor agonists inhibit locomotor activity and induce catalepsy in rodents [Adv. Neurol., 80, 121-123 (1999); and Psychopharmacology, 147, 90-95 (1999)]. In contrast, adenosine $A_{2A}$ receptor antagonists prevent the motor disturbances of dopamine $D_2$ receptor null mice [J. Neurosci., 20, 5848-5852 (2000)].

$A_{2A}$ receptor antagonists have been evaluated in parkinsonian monkeys and found to be effective at treating symptoms of Parkinson's disease [Ann. Neurol., 43, 507-513 (1998); NeuroReport, 9, 2857-2860 (1998); and Exp. Neurol., 162, 321-327 (2000)]. It was demonstrated that the adenosine $A_{2A}$ receptor antagonist KW-6002 exhibits antiparkinsonian activity without producing hyperactivity and provoking dyskinesia [Neurology, 52, 1673-1677 (1999)].

More recently, the neuroprotective effect of an adenosine $A_{2A}$ receptor antagonist KW-6002 has been demonstrated in MPTP-induced dopaminergic neurodegeneration [J. Neurochem., 80, 262-270 (2002); and J. Neurosci., 21, RC143(1-6) (2001)].

SUMMARY OF THE INVENTION

The present invention relates to methods of treating restless legs syndrome or related disorders by administering a pharmaceutical agent containing a therapeutically effective amount of an adenosine $A_{2A}$ receptor antagonist to a patient in need thereof. The present invention also relates to use of an adenosine $A_{2A}$ receptor antagonist for manufacturing a therapeutic agent for treatment of restless legs syndrome as well as to therapeutic agents for restless legs syndrome comprising an adenosine $A_{2A}$ receptor antagonist.

Preferably the adenosine $A_{2A}$ receptor antagonist is a xanthine derivative or a pharmaceutically acceptable salt thereof.

More preferably, the adenosine $A_{2A}$ receptor antagonist is a xanthine derivative or a pharmaceutically acceptable salt thereof described in detail herein.

DETAILED DESCRIPTION OF THE INVENTION

The present invention relates to the following (1) to (26).

(1) A method of treating restless legs syndrome, comprising administrating an effective amount of at least one adenosine $A_{2A}$ receptor antagonist to a patient in need thereof.

(2) The method of treating restless legs syndrome according to the above (1) wherein the adenosine $A_{2A}$ receptor antagonist is a xanthine derivative or a pharmaceutically acceptable salt thereof.

(3) The method of treating restless legs syndrome according to the above (2) wherein the xanthine derivative is represented by the following formula (I):

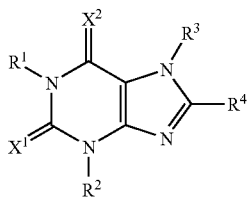

(I)

wherein $R^1$, $R^2$, and $R^3$ independently represent hydrogen, lower alkyl, lower alkenyl, or lower alkynyl; $R^4$ represents cycloalkyl, —(CH$_2$)—R$^5$ (in which R$^5$ represents substituted or unsubstituted aryl, or a substituted or unsubstituted heterocyclic group; and n is an integer of 0 to 4) or

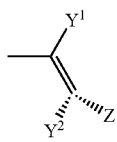

{in which $Y^1$ and $Y^2$ independently represent hydrogen, halogen or lower alkyl; and Z represents substituted or unsubstituted aryl, or

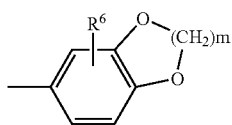

(in which $R^6$ represents hydrogen, hydroxy, lower alkyl, lower alkoxy, halogen, nitro or amino; and m represents an integer of 1 to 3)}; and $X^1$ and $X^2$ independently represent O or S.

(4) The method of treating restless legs syndrome according to the above (2) wherein the xanthine derivative is represented by the following formula (I-A):

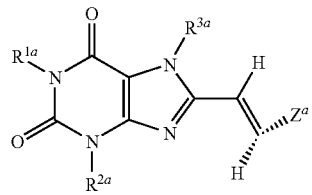

(I-A)

wherein $R^{1a}$ and $R^{2a}$ independently represent methyl or ethyl; $R^{3a}$ represents hydrogen or lower alkyl; and $Z^a$ represents

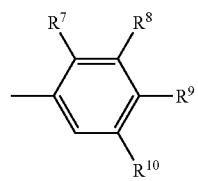

(in which at least one of $R^7$, $R^8$ and $R^9$ represents lower alkyl or lower alkoxy and the others represent hydrogen; $R^{10}$ represents hydrogen or lower alkyl) or

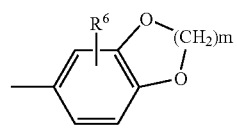

(in which $R^6$ and m have the same meanings as defined above, respectively).

(5) The method of treating restless legs syndrome according to the above (2) wherein the xanthine derivative is represented by the following formula (I-B):

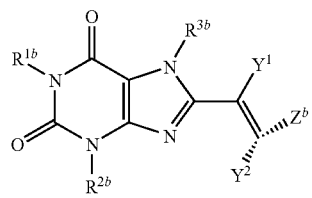

(I-B)

wherein $R^{1b}$ and $R^{2b}$ independently represent hydrogen, propyl, butyl, lower alkenyl or lower alkynyl; $R^{3b}$ represents hydrogen or lower alkyl; $Z^b$ represents substituted or unsubstituted naphthyl, or

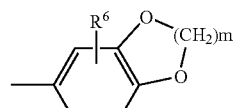

(in which $R^6$ and m have the same meanings as defined above, respectively); and $Y^1$ and $Y^2$ have the same meanings as defined above, respectively.

(6) The method of treating restless legs syndrome according to the above (2) wherein the xanthine derivative is (E)-8-(3,4-dimethoxystyryl)-1,3-diethyl-7-methylxanthine.

(7) The method of treating restless legs syndrome according to the above (1) wherein the adenosine $A_{2A}$ receptor antagonist is a compound represented by the formula (II):

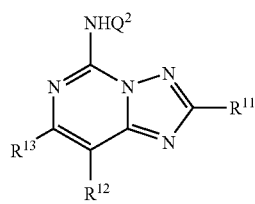

(II)

wherein $R^{11}$ represents substituted or unsubstituted aryl, or a substituted or unsubstituted heterocyclic group; $R^{12}$ represents hydrogen, halogen, lower alkyl, substituted or unsubstituted aryl, or a substituted or unsubstituted heterocyclic group; $R^{13}$ represents hydrogen, halogen or $X^2R^{14}$ (in which $X^2$ represents O or S; and $R^{14}$ represents substituted or unsubstituted lower alkyl, substituted or unsubstituted aryl, a substituted or unsubstituted heterocyclic group, or substituted or unsubstituted aralkyl); and $Q^2$ represents hydrogen or 3,4-dimethoxybenzyl {e.g. 5-amino-7-(4-benzoylpiperazinyl)-2-(2-furyl)[1,2,4]triazolo[1,5-c]pyrimidine}, or a pharmaceutically acceptable salt thereof.

(8) The method of treating restless legs syndrome according to the above (1) wherein the adenosine $A_{2A}$ receptor antagonist is a compound represented by the formula (III):

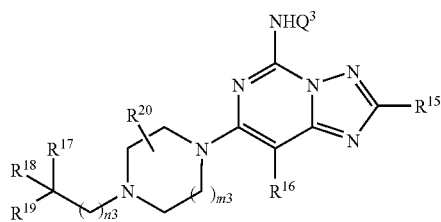

(III)

wherein $R^{15}$ represents substituted or unsubstituted aryl, or substituted or unsubstituted heteroaryl; $R^{16}$ represents hydrogen, halogen, substituted or unsubstituted lower alkyl, substituted or unsubstituted aryl, or substituted or unsubstituted heteroaryl; m3 and n3 are independently an integer of 0 to 4; $Q^3$ represents hydrogen or 3,4-dimethoxybenzyl; $R^{20}$ represents hydrogen, halogen, hydroxy, or substituted or unsubstituted lower alkyl; $R^{17}$ represents hydroxy, hydroxy-substituted lower alkyl, substituted or unsubstituted lower alkoxy, or imidazo[1,2-a]pyridyl; and $R^{18}$ and $R^{19}$ independently represent hydrogen, substituted or unsubstituted lower alkyl, or substituted or unsubstituted aryl; or $R^{18}$ and $R^{19}$ are combined together with an adjacent carbon atom to form a substituted or unsubstituted cycloalkyl {e.g. 5-amino-2-(2-furyl)-7-(4-(2-hydroxy-2-methylpropyl)piperazinyl)[1,2,4]triazolo[1,5-c]pyrimidine}, or a pharmaceutically acceptable salt thereof.

(9) The method of treating restless legs syndrome according to the above (1) wherein the adenosine $A_{2A}$ receptor antagonist is a compound represented by the formula (IV):

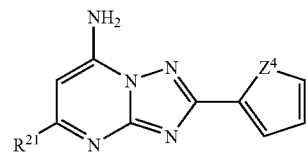

(IV)

wherein $Z^4$ represents O or S; and $R^{21}$ represents Ph—$(CH_2)_{n4}Y^4$ (in which Ph represents phenyl unsubstituted or substituted with halogen or lower alkyl; $Y^4$ is a single bond, O or S; and n4 is an integer of 0 to 5) {e.g. 7-amino-2-(2-furyl)-5-phenoxy[1,2,4]-triazolo[1,5-a]pyrimidine}, or a pharmaceutically acceptable salt thereof.

(10) The method of treating restless legs syndrome according to the above (1) wherein the adenosine $A_{2A}$ receptor antagonist is a compound represented by the formula (V):

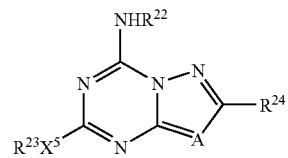

(V)

wherein $R^{22}$ represents hydrogen, substituted or unsubstituted lower alkyl, or substituted or unsubstituted lower alkanoyl; $R^{23}$ represents hydrogen, substituted or unsubstituted lower alkyl, substituted or unsubstituted lower alkenyl, substituted or unsubstituted cycloalkyl, substituted or unsubstituted aryl, substituted or unsubstituted aralkyl, or a substituted or unsubstituted heterocyclic group; $R^{24}$ represents a substituted or unsubstituted heterocyclic group; $X^5$ represents a single bond, O, S, S(O), $S(O)_2$ or $NR^{25}$ (in which $R^{25}$ represents hydrogen, or substituted or unsubstituted lower alkyl); and A represents N or $CR^{26}$ (in which $R^{26}$ represents hydrogen, or substituted or unsubstituted lower alkyl), or a pharmaceutically acceptable salt thereof.

(11) The method of treating restless legs syndrome according to the above (1) wherein the adenosine $A_{2A}$ receptor antagonist is a compound represented by the formula (VI):

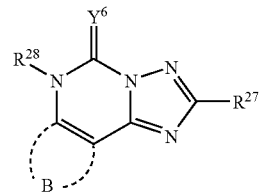

(VI)

wherein $R^{27}$ represents substituted or unsubstituted aryl, or a substituted or unsubstituted heterocyclic group; $Y^6$ represents O, S or $NR^{29}$ (in which $R^{29}$ represents hydrogen, substituted or unsubstituted lower alkyl, substituted or unsubstituted cycloalkyl, or substituted or unsubstituted aryl); $R^{28}$ represents hydrogen, substituted or unsubstituted lower alkyl, substituted or unsubstituted lower alkenyl, substituted or unsubstituted lower alkynyl, substituted or unsubstituted cycloalkyl, substituted or unsubstituted aryl, substituted or unsubstituted aralkyl, or a substituted or unsubstituted heterocyclic group; and B and the adjacent two carbon atoms are combined to form a substituted or unsubstituted carbon ring or heterocyclic ring, or a pharmaceutically acceptable salt thereof.

(12) The method of treating restless legs syndrome according to the above (1) wherein the adenosine $A_{2A}$ receptor antagonist is a compound represented by the formula (VII):

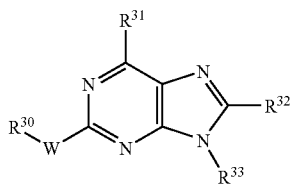

(VII)

wherein $R^{30}$ represents substituted or unsubstituted lower alkyl, or substituted or unsubstituted aryl; W represents $CH_2CH_2$, $CH=CH$ or $CC$; $R^{31}$ represents hydrogen, hydroxy, substituted or unsubstituted lower alkyl, substituted or unsubstituted amino, or a substituted or unsubstituted heterocyclic group; $R^{32}$ represents hydrogen, substituted or unsubstituted cycloalkyl, substituted or unsubstituted aryl, substituted or unsubstituted heteroaryl, or substituted or unsubstituted lower alkenyl; and $R^{33}$ represents hydrogen, substituted or unsubstituted lower alkyl, substituted or unsubstituted cycloalkyl, substituted or unsubstituted aryl, substituted or unsubstituted heteroaryl, substituted or unsubstituted lower alkenyl, or substituted or unsubstituted lower alkynyl {e.g. 4-[6-amino-8-(3-fluorophenyl)-9-methyl-9H-2-fluorenyl]-2-methyl-3-butyn-2-ol}, or a pharmaceutically acceptable salt thereof.

(13) The method of treating restless legs syndrome according to the above (1) wherein the adenosine $A_{2A}$ receptor antagonist is a compound represented by the formula (VIII):

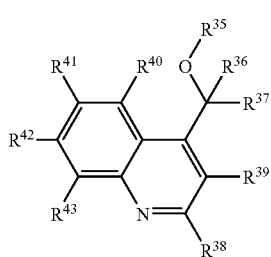

(VIII)

wherein $R^{35}$ represents hydrogen or lower alkyl; $R^{36}$ and $R^{37}$ independently represent hydrogen, substituted or unsubstituted lower alkyl, or substituted or unsubstituted aryl; and $R^{38}$, $R^{39}$, $R^{40}$, $R^{41}$, $R^{42}$, and $R^{43}$, independently represent hydrogen, substituted or unsubstituted lower alkyl, substituted or unsubstituted aryl, or a substituted or unsubstituted heterocyclic group, or a pharmaceutically acceptable salt thereof.

(14) The method of treating restless legs syndrome according to the above (1) wherein the adenosine $A_{2A}$ receptor antagonist is a compound represented by the formula (IX):

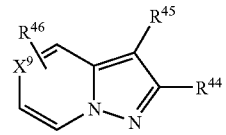

(IX)

wherein $X^9$ represents CH or N; $R^{44}$ represents lower alkyl, substituted or unsubstituted aryl, or a substituted or unsubstituted heterocyclic group; $R^{45}$ represents substituted or unsubstituted lower alkyl, or a substituted or unsubstituted heterocyclic group; and $R^{46}$ represents hydroxy, halogen, or substituted or unsubstituted lower alkyl {e.g. 3-[2-(thiazol-2-ylmethyl)-3-oxo-2,3-dihydropyridazin-6-yl]-2-phenylpyrazolo[1,5-a]pyridine}, or a pharmaceutically acceptable salt thereof.

(15) The method of treating restless legs syndrome according to the above (1) wherein the adenosine $A_{2A}$ receptor antagonist is a compound represented by the formula (X):

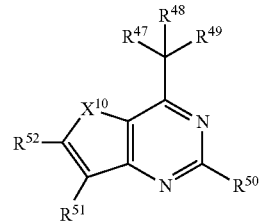

(X)

wherein $X^{10}$ represents O or S; $R^{47}$ and $R^{48}$ independently represent hydrogen, lower alkyl, aryl, hydroxy, alkoxy, cyano or nitro, or together form a carbonyl, oxime, imino or hydrazone group; $R^{49}$ represents lower alkyl or aryl; and $R^{50}$, $R^{51}$ and $R^{52}$ independently represent hydroxy, halogen, substituted or unsubstituted lower alkyl, substituted or unsubstituted aryl, nitro, cyano or alkoxy {e.g. (2R)-2-(1-hydroxy-2-propylamino)thieno[3,2-d]pyrimidin-4-yl 2-thienylmethanone}, or a pharmaceutically acceptable salt thereof.

(16) The method of treating restless legs syndrome according to the above (1) wherein the adenosine $A_{2A}$ receptor antagonist is a compound represented by the formula (XI):

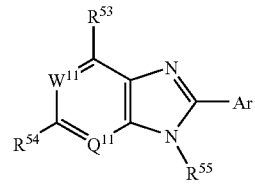

(XI)

wherein $R^{53}$ represents hydrogen, hydroxy, halogen, substituted or unsubstituted amino, or substituted or unsubstituted lower alkyl; $R^{54}$ represents hydrogen, halogen, substituted or unsubstituted amino, substituted or unsubstituted lower alkynyl, substituted or unsubstituted lower alkenyl, substituted or unsubstituted lower alkyl, or substituted or unsubstituted lower alkoxy; $R^{55}$ represents substituted or unsubstituted lower alkyl, substituted or unsubstituted aryl, or substituted or unsubstituted heteroaryl; Ar represents substituted or unsubstituted aryl, or substituted or unsubstituted heteroaryl; and $Q^{11}$ and $W^{11}$ independently represent N or CH {e.g. 5-[6-amino-8-(3-fluorophenyl)-9H-9-purinyl]-1-methyl-1,2-dihydro-2-pyrimidine}, or a pharmaceutically acceptable salt thereof.

(17) The method of treating restless legs syndrome according to the above (1) wherein the adenosine $A_{2A}$ receptor antagonist is a compound represented by the formula (XII):

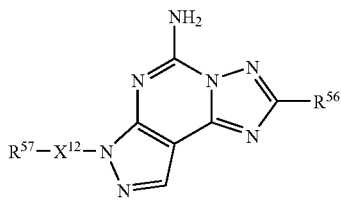

(XII)

wherein $R^{56}$ represents substituted or unsubstituted aryl, substituted or unsubstituted cycloalkenyl, or substituted or unsubstituted heteroaryl; $X^{12}$ represents a single bond or C(O); and $R^{57}$ represents substituted or unsubstituted lower alkyl, or a pharmaceutically acceptable salt thereof.

(18) The method of treating restless legs syndrome according to the above (1) wherein the adenosine $A_{2A}$ receptor antagonist is a compound represented by the formula (XIII):

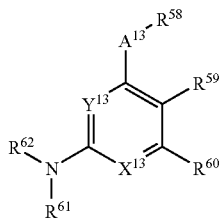

(XIII)

wherein $A^{13}$ represents a single bond, —S—, —N($R^{63}$)— (in which $R^{63}$ represents hydrogen or lower alkyl), —(CH$_2$)$_2$—, —CH=CH—, —CC— or —O—; $X^{13}$ and $Y^{13}$ independently represents N or CH; $R^{58}$ represents hydrogen, substituted or unsubstituted lower alkyl, lower alkenyl, lower alkynyl, halogen, cyano or cycloalkyl; $R^{59}$ represents hydrogen, halogen, cyano, nitro, substituted or unsubstituted lower alkyl, lower alkenyl, or substituted or unsubstituted aryl; $R^{60}$ represents lower alkyl, substituted or unsubstituted aryl, or substituted or unsubstituted heteroaryl; and $R^{61}$ and $R^{62}$ independently represent hydrogen, or substituted or unsubstituted aryl, or a pharmaceutically acceptable salt thereof.

(19) The method of treating restless legs syndrome according to the above (1) wherein the adenosine $A_{2A}$ receptor antagonist is a compound represented by the formula (XIV):

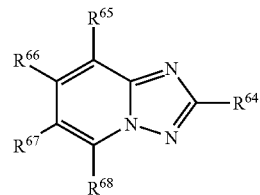

(XIV)

wherein $R^{64}$ represents substituted or unsubstituted lower alkoxy, substituted or unsubstituted aryl, or substituted or unsubstituted heteroaryl; $R^{65}$ and $R^{67}$ independently represent hydrogen, cyano or S(O)$_2$phenyl; $R^{66}$ represents hydrogen, halogen, substituted or unsubstituted aryl, substituted or unsubstituted heteroaryl, or substituted or unsubstituted amino; and $R^{68}$ represents substituted or unsubstituted amino {e.g. 2-(4,5-dihydro-furan-2-yl)-7-m-tolyl-[1,2,4]triazolo[1,5-a]pyridine-5-ylamine}, or a pharmaceutically acceptable salt thereof.

(20) The method of treating restless legs syndrome according to the above (1) wherein the adenosine $A_{2A}$ receptor antagonist is a compound represented by the formula (XV):

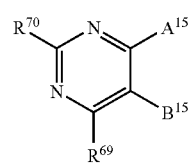

(XV)

wherein $A^{15}$ represents substituted or unsubstituted aryl, or substituted or unsubstituted heteroaryl; $B^{15}$ represents substituted or unsubstituted heteroaryl; $R^{69}$ and $R^{70}$ independently represent hydrogen, or substituted or unsubstituted amino, or a pharmaceutically acceptable salt thereof.

(21) The method of treating restless legs syndrome according to the above (1) wherein the adenosine $A_{2A}$ receptor antagonist is a compound represented by the formula (XVI):

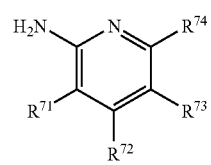

(XVI)

wherein $R^{71}$ represents cyano, carboxy, or substituted or unsubstituted carbamoyl; $R^{72}$ represents hydrogen, hydroxy, substituted or unsubstituted lower alkoxy, substituted or unsubstituted aryl, or substituted or unsubstituted heteroaryl; and $R^{73}$ and $R^{74}$ independently represent substituted or unsubstituted aryl, or a substituted or unsubstituted heterocyclic group, or a pharmaceutically acceptable salt thereof.

(22) The method of treating restless legs syndrome according to the above (1) wherein the adenosine $A_{2A}$ receptor antagonist is a compound represented by the formula (XVII):

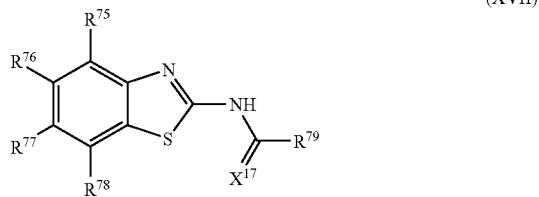

wherein $R^{75}$ represents hydrogen, hydroxy, halogen, lower alkyl, lower alkoxy, benzyloxy or $OCF_3$; $R^{76}$ and $R^{77}$ independently represent hydroxy, halogen, lower alkyl or lower alkoxy; $R^{78}$ represents hydrogen, halogen, lower alkyl, lower alkenyl, carboxy, lower alkanoyl, lower alkoxycarbonyl, $(CH_2)_{n17}$—OH (in which n17 is an integer of 0 to 4), substituted or unsubstituted phenyl, 2,3-dihydro-1H-indolyl, azepan-1-yl or 1,4-oxazepan-4-yl; $R^{79}$ represents substituted or unsubstituted phenyl; and $X^{17}$ represents O, S or 2H {e.g. 4-hydroxymethyl-N-(4-methoxy-7-phenyl-benzothiazol-2-yl)benzamide}, or a pharmaceutically acceptable salt thereof.

(23) The method of treating restless legs syndrome according to the above (1) wherein the adenosine $A_{2A}$ receptor antagonist is (−)-(11S,2′R)-α-2-piperidinyl-2,8-bis (trifluoromethyl)-4-quinolinemethanol or a pharmaceutically acceptable salt thereof.

(24) Use of the adenosine $A_{2A}$ receptor antagonist described in any one of the above (1) to (23) for manufacturing a therapeutic agent for restless legs syndrome.

(25) A therapeutic agent for restless legs syndrome comprising the adenosine $A_{2A}$ receptor antagonist described in any one of the above (1) to (23).

(26) A method of treating nocturnal myoclonus, comprising administrating an effective amount of the adenosine $A_{2A}$ receptor antagonist described in any one of the above (1) to (23) to a patient in need thereof.

The adenosine $A_{2A}$ receptor antagonist used in the method of the present invention is not limited as long as it has $A_{2A}$ receptor antagonistic activity. $A_{2A}$ receptor antagonistic activity includes activity to inhibit, suppress or cause the cessation of at least one adenosine-mediated biological activity by, e.g., binding to adenosine $A_{2A}$ receptors, or interfering with or preventing the binding of adenosine to the receptor. Examples of the adenosine $A_{2A}$ receptor antagonist include compounds disclosed in U.S. Pat. No. 5,484,920, U.S. Pat. No. 5,703,085, WO 92/06976, WO 94/01114, U.S. Pat. No. 5,565,460, WO 98/42711, WO 00/17201, WO 99/43678, WO 99/26627, WO 01/92264, WO 99/35147, WO 00/13682, WO 00/13681, WO 00/69464, WO 01/40230, WO 01/02409, WO 01/02400, EP 1054012, WO 01/62233, WO 01/17999, WO 01/80893, WO 02/14282, WO 01/97786, or the like. More specifically, examples include compounds represented by the above-described formula (I), (I-A), (I-B), or (II) to (XVII), (−)-(11S,2′R)-α-2-piperidinyl-2,8-bis(trifluoromethyl)-4-quinolinemethanol, and pharmaceutically acceptable salts thereof.

A preferred adenosine $A_{2A}$ receptor antagonist used in the method of the present invention is (E)-8-(3,4-dimethoxystyryl)-1,3-diethyl-7-methylxanthine (hereinafter referred to Compound A) shown below.

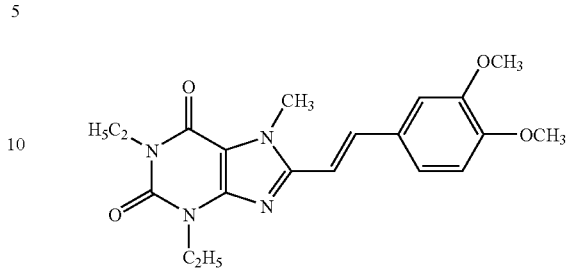

In the definition of each group of formulas (I), (I-A), (I-B), and (II) to (XVII), the lower alkyl and the lower alkyl moiety of the lower alkoxy, hydroxy-substituted lower alkyl, lower alkanoyl, and lower alkoxycarbonyl include straight-chain or branched alkyl groups having 1 to 8 carbon atoms, such as methyl, ethyl, propyl, isopropyl, butyl, isobutyl, sec-butyl, tert-butyl, pentyl, neopentyl, hexyl, heptyl and octyl. The lower alkenyl includes straight-chain or branched alkenyl groups having 2 to 8 carbon atoms, such as vinyl, allyl, methacryl, crotyl, 3-butenyl, 2-pentenyl, 4-pentenyl, 2-hexenyl, 5-hexenyl, 2-heptenyl and 2-octenyl. The lower alkynyl includes straight-chain or branched alkynyl groups having 2 to 8 carbon atoms, such as ethynyl, propargyl, 2-butynyl, 3-butynyl, 2-pentynyl, 4-pentynyl, 2-hexynyl, 5-hexynyl, 4-methyl-2-pentynyl, 2-heptynyl and 2-octynyl. The cycloalkyl includes cycloalkyl groups having 3 to 8 carbon atoms, such as cyclopropyl, cyclobutyl, cyclopentyl, cyclohexyl, cycloheptyl and cyclooctyl. The cycloalkenyl includes cycloalkenyl groups having 4 to 8 carbon atoms, such as cyclobutenyl, cyclopentenyl, cyclohexenyl, cycloheptenyl and cyclooctenyl. The aryl includes those having 6 to 14 carbon atoms, such as phenyl and naphthyl. The aralkyl includes those having 7 to 15 carbon atoms, such as benzyl, phenethyl, benzhydryl and naphthylmethyl. Examples of the heteroaryl are furyl, thienyl, pyrrolyl, pyranyl, thiopyranyl, pyridyl, thiazolyl, imidazolyl, pyrimidyl, pyridazinyl, pyridazinoyl, triazinyl, indolyl, quinolyl, purinyl and benzothiazolyl. Examples of the heterocyclic group are pyrrolidinyl, piperidino, piperidinyl, piperazinyl, morpholino, morpholinyl, thiomorpholino, thiomorpholinyl, homopiperidino, homopiperidinyl, homopiperazinyl, tetrahydropyridinyl, tetrahydroquinolinyl, tetrahydroisoquinolinyl, tetrahydrofuranyl, tetrahydropyranyl, imidazolidinyl, thiazolidinyl and oxazolidinyl in addition to groups listed as examples of the heteroaryl. The halogen includes fluorine, chlorine, bromine and iodine. The carbon ring formed by combining B and the adjacent two carbons include those having 4 to 8 carbon atoms and at least one double bond, such as cyclobutene, cyclopentene, cyclohexene, cycloheptene and cyclooctene. Examples of the heterocyclic ring formed by combining B and the adjacent two carbons are pyrrole, pyrane, thiopyrane, pyridine, thiazole, imidazole, pyrimidine, triazine, indole, quinoline, benzothiazole, pyrroline, tetrahydropyridine, tetrahydropyrazine, tetrahydroquinoline and tetrahydroisoquinoline.

The substituted lower alkyl, the substituted lower alkoxy, the substituted lower alkanoyl and the substituted lower alkenyl each have, for example, 1 to 3 independently selected substituents. Examples of the substituents are hydroxy, substituted or unsubstituted lower alkoxy, halogen, nitro, amino, lower alkylamino, di(lower alkyl) amino, trifluoromethyl, trifluoromethoxy, benzyloxy, phenyl and phenoxy. The lower alkyl and the alkyl moiety of the lower alkoxy, lower alkylamino and di(lower alkyl)amino have the same meaning as the lower alkyl defined above. The halogen has the same meaning as the halogen defined above. Examples of the substituent of the substituted lower alkoxy are hydroxy, lower alkoxy, halogen, amino, azide, carboxy and lower alkoxycarbonyl. The lower alkyl moiety of the lower alkoxy and lower alkoxycarbonyl has the same meaning as the lower alkyl defined above, and the halogen has the same meaning as the halogen defined above.

The substituted aryl, the substituted naphthyl, the substituted phenyl, the substituted aralkyl, the substituted heterocyclic ring, the substituted heteroaryl, the substituted cycloalkyl, the substituted cycloalkenyl, the substituted carbon ring formed by combining B and the adjacent two carbons, and the substituted heterocyclic ring formed by combining B and the adjacent two carbons each have, for example, 1 to 4 independently selected substituents. Examples of the substituents are lower alkyl, hydroxy, substituted or unsubstituted lower alkoxy, halogen, nitro, amino, lower alkylamino, di(lower alkyl)amino, trifluoromethyl, trifluoromethoxy, benzyloxy, phenyl and phenoxy. The lower alkyl and the alkyl moiety of the lower alkoxy, lower alkylamino and di(lower alkyl)amino have the same meaning as the lower alkyl defined above. The halogen has the same meaning as the halogen defined above. Examples of the substituent of the substituted lower alkoxy are hydroxy, lower alkoxy, halogen, amino, azide, carboxy and lower alkoxycarbonyl. The lower alkyl moiety of the lower alkoxy and lower alkoxycarbonyl has the same meaning as the lower alkyl defined above, and the halogen has the same meaning as the halogen defined above.

The substituted amino and the substituted carbamoyl each have 1 or 2 independently selected substituents. Examples of the substituents are substituted or unsubstituted lower alkyl, or substituted or unsubstituted lower alkoxy. The lower alkyl and the alkyl moiety of the lower alkoxy have the same meaning as the lower alkyl defined above. Examples of the substituent of the substituted lower alkyl and the substituted lower alkoxy are hydroxy, lower alkoxy, halogen, amino, azide, carboxy and lower alkoxycarbonyl. The lower alkyl moiety of the lower alkoxy and lower alkoxycarbonyl has the same meaning as the lower alkyl defined above, and the halogen has the same meaning as the halogen defined above.

Hereinafter, compounds represented by formulas (I), (I-A), (I-B), and (II) to (XVII) will be referred to as Compounds (I), (I-A), (I-B), and (II) to (XVII), respectively.

The pharmaceutically acceptable salts of Compounds (I), (I-A), (I-B), and (II) to (XVII) include pharmaceutically acceptable acid addition salts, metal salts, ammonium salts, organic amine addition salts and amino acid addition salts.

The pharmaceutically acceptable acid addition salts include inorganic acid addition salts such as hydrochloride, sulfate, nitrate and phosphate, and organic acid addition salts such as acetate, maleate, fumarate and citrate; the pharmaceutically acceptable metal salts include alkali metal salts such as sodium salt and potassium salt, alkaline earth metal salts such as magnesium salt and calcium salt, aluminium salt and zinc salt; the pharmaceutically acceptable ammonium salts include ammonium and tetramethylammonium; the pharmaceutically acceptable organic amine addition salts include addition salts with morpholine or piperidine; and the pharmaceutically acceptable amino acid addition salts include addition salts with lysine, glycine or phenylalanine.

Compounds (I), (I-A), (I-B), and (II) to (XVII), and pharmaceutically acceptable salts thereof can be produced in accordance with the methodology described in U.S. Pat. No. 5,484,920, U.S. Pat. No. 5,703,085, WO 92/06976, WO 94/01114, U.S. Pat. No. 5,565,460, WO 98/42711, WO 00/17201, WO 99/43678, WO 99/26627, WO 01/92264, WO 99/35147, WO 00/13682, WO 00/13681, WO 00/69464, WO 01/40230, WO 01/02409, WO 01/02400, EP 1054012, WO 01/62233, WO 01/17999, WO 01/80893, WO 02/14282, WO 01/97786 or the like.

Pharmaceutical compositions for administration according to the present invention comprise at least one adenosine $A_{2A}$ receptor antagonist as active ingredient(s) optionally combined with a pharmaceutically acceptable carrier(s). These compositions can be administered by any means that achieve their intended purposes. Amounts and regimens for the administration of a composition according to the present invention can be readily determined by those with ordinary skill in the art in treating patients suffering from RLS.

The pharmaceutical compositions described herein can be administered by any suitable method including, without limitation, orally; intranasally; intrapulmonarily; parenterally, such as subcutaneously, intravenously, intramuscularly, intraperitoneally; intraduodenally; transdermally; or buccally.

The dosage administered is an effective amount and depends upon the age, health and weight of the patient, type of previous or concurrent treatment, if any, frequency of treatment, and the nature of the effect desired. Several factors are typically taken into account when determining an appropriate dosage. These factors include age, sex and weight of the patient, the condition being treated, the severity of the condition and the form of the drug being administered.

An "effective amount" is an amount sufficient to effect a beneficial or desired clinical result. An effective amount can be administered in one or more doses. In terms of treatment, an effective amount is amount that is sufficient to palliate, ameliorate, stabilize, reverse or slow the progression of the disease or disorder, or otherwise reduce the pathological consequences of the disease or disorder. The effective amount is generally determined by the physician on a case-by-case basis and is within the skill of one in the art.

In addition to the active ingredient(s), the pharmaceutical compositions according to the present invention can also contain a suitable pharmaceutically acceptable carrier such as an excipient that facilitates processing of the active ingredient(s) into a pharmaceutically acceptable preparation. Preferably, the preparations, particularly those preparations which can be administered orally and which can be used for the preferred type of administration, such as tablets, troches and capsules, and also preparations which can be administered rectally, such as suppositories, as well as suitable solutions for administration by injection or oral administration, contain from about 0.1 to 99 percent, preferably from about 20 to 85 percent of active ingredient(s), together with the excipient. Liquid preparations can, for example, be prepared by dissolving or dispersing a compound embodied herein in a liquid excipient, such as water, saline, aqueous dextrose, glycerol, or ethanol. The pharmaceutical composition can also contain other medicinal agent(s), pharmaceutical agent(s), carrier(s), or auxiliary substance(s) such as wetting or emulsifying agent(s), or pH buffering agent(s).

Pharmaceutical compositions according to the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions according to the present invention for human use are typically administered orally.

Pharmaceutical compositions for oral, intranasal, or topical administration can be supplied in solid, semi-solid or liquid forms, including tablets, capsules, powders, liquids, and suspensions. Pharmaceutical compositions for injection can be supplied as liquid solutions or suspensions, as emulsions, or as solid forms suitable for dissolution or suspension in liquid prior to injection. For administration via the respiratory tract, a preferred pharmaceutical composition is one that provides a solid, powder, or liquid aerosol when used with an appropriate aerosolizer device. Although not required, pharmaceutical compositions are preferably supplied in unit dosage form suitable for administration of a precise amount. Also contemplated by the present invention are slow release or sustained release forms, whereby relatively consistent levels of the active ingredient(s) are provided over an extended period.

The adenosine $A_{2A}$ receptor antagonists may preferably be administered in an amount of from about 0.001 to about 20.0 mg per kilogram of body weight. A dosage range of from about 0.01 to about 10 mg per kilogram of body weight is more preferable. Since the adenosine $A_{2A}$ receptor antagonists used in the present invention will eventually be cleared from the bloodstream, re-administration of the pharmaceutical compositions is indicated and preferred.

The adenosine $A_{2A}$ receptor antagonists can be administered in a manner compatible with the dosage formulation and in such an amount as will be therapeutically effective. Systemic dosages depend on the age, weight and conditions of the patient and on the administration route.

Pharmaceutical preparations useful in the methods according to the present invention are manufactured in a known manner. The preparation of pharmaceutical compositions is conducted in accordance with generally accepted procedures for the preparation of pharmaceutical preparations [e.g., Remington's Pharmaceutical Sciences $18^{th}$ Edition (1990), E. W. Martin ed., Mack Publishing Co., Pa]. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units, and enclosing in a delivery device.

The pharmaceutical preparations for oral use can be obtained by combining the active ingredient(s) with solid excipient(s), optionally grinding the resulting mixture, and processing the mixture of granules, after adding suitable auxiliarie(s), if desired or necessary, to obtain tablets.

Suitable excipients include fillers such as saccharides, for example, lactose, sucrose, mannitol or sorbitol; cellulose derivatives; zinc compounds; and/or calcium phosphates such as tricalcium phosphate or calcium hydrogen phosphates; binders such as starch paste, using, for example, maize starch, wheat starch, rice starch or potato starch; gelatin; tragacanth; and/or polyvinylpyrrolidone.

Auxiliaries include flow-regulating agents and lubricants, such as silica, talc, stearic acid or salts thereof, and/or polyethylene glycol. Tablet, caplet or capsule cores are provided with suitable coatings which, if desired, are resistant to gastric juices. For this purpose, concentrated saccharide solutions can be used, which can optionally contain gum Arabic, talc, polyvinyl pyrrolidone, polyethylene glycol and/or titanium dioxide, lacquer solutions and suitable organic solvents or solvent mixtures. In order to produce coatings resistant to gastric juices, i.e., enteric coatings, solutions of suitable cellulose preparations such as acetylcellulose phthalate or hydroxypropyl methyl cellulose phthalate are used. Dyes or pigments can be added to the tablets or coatings, for example, for identification or in order to characterize combinations of active compound doses.

Other pharmaceutical preparations, which can be used orally, include push-fit capsules made of gelatin, as well as soft, sealed capsules made of gelatin and a plasticizer such as glycerol or sorbitol. The push-fit capsules can contain the active ingredient(s) in the form of granules, which can be mixed with filler(s) such as lactose, binders such as starches, and/or lubricant(s) such as talc or magnesium stearate and, optionally, stabilizer(s). In soft capsules, the active ingredient(s) are preferably dissolved or suspended in suitable liquids, such as fatty oils or liquid paraffin. In addition, stabilizer(s) may be added.

The adenosine $A_{2A}$ receptor antagonists of the present invention can also be administered in the form of an implant when compounded with a biodegradable slow-release carrier. Alternatively, the active ingredients can be formulated as a transdermal patch for continuous release of the active ingredient(s). Methods of making implants and patches are well known in the art [Remington's Pharmaceutical Sciences $18^{th}$ Edition (1990), E. W. Martin ed., Mack Publishing Co., Pa; and Kydonieus ed. (1992) Treatise on controlled drug delivery Marcel Dekker, NY].

The following non-limiting Examples, further illustrate the present invention. All references cited herein are hereby incorporated by reference.

Example 1

Animal Model, RLS Treatment with an $A_{2A}$ Receptor Antagonist

Compound A, a novel potent adenosine $A_{2A}$ receptor antagonist has been proved efficacious in ameliorating Parkinsonian symptoms in animal models and in an early Phase II studies in patients with advanced Parkinson's disease. The ability of Compound A to interact with the midbrain dopaminergic and GABAergic systems provides a basis for treating RLS.

It is reported that bilateral 6-OHDA lesions into the A11 nucleus elicited behavioral correlates similar to clinical conditions of RLS, that is, increased average number of standing episodes and increased total standing time [Ondo et al., Mov. Dis., 15, 154-158 (2000)]. Notably, treatment of the lesioned animals with a dopamine agonist, pramipexole, subsequently resulted in fewer standing episodes and less total standing time. These findings are consistent with what would be expected in an animal model of RLS.

In order to determine the effectiveness of $A_{2A}$ antagonists in the RLS animal model system, the method according to Ondo et al. (2000) is used. Anesthetized rats are stereotaxically injected with approximately 8 μg of 6-OHDA dissolved in phosphate-buffered saline (PBS) containing 0.01-0.05 w/v % ascorbic acid into both right and left A11 nuclei. Control rats are similarly injected with vehicle without 6-OHDA.

Two to 12 weeks after 6-OHDA or vehicle injection, animals are observed for 30-120 minutes and their behaviors are scored in terms of number of times standing on two legs and total amount of time on two legs. Duration of total sleep time may also be measured. Introduction of electroencephalography or electromyography further helps elucidate the behavior characteristics of the animals, lesioned or not. Effects of pharmacological manipulation on the lesioned animals are subsequently assessed. Administration of adenosine $A_{2A}$ receptor antagonists counteracts the altered behaviors observed in the lesioned animals. Vehicle- or pramipexole-treatment lesioned animals serve as a negative or positive control, respectively.

After the completion of behavioral tests and drug or control treatment, rats are sacrificed and their whole brains are removed. Coronal sections of diencephalic regions containing A11 groups are cut in a cryostat and the sections obtained are subsequently processed to tyrosine hydroxylase (TH) immunohistochemistry. Stained sections are observed under the light microscope to confirm the proper lesion of A11 nuclei. The results of controls compared to $A_{2A}$ antagonist are compared in light of the lesion results.

Example 2

Human Clinical Trial, RLS Treatment with an $A_{2A}$ Antagonist

This study evaluates the efficacy of Compound A in RLS. A total of 45 patients diagnosed with moderate to severe idiopathic RLS and PLMS are allocated into 3 groups. Patients who have failed to respond to one or combined treatment are not eligible for this study. The baseline RLS and PLMS symptoms are evaluated by a patient-administered visual analog scale, the clinician's global impression scale (CGI), and polysomnograph. Patients in the first group receive 5 mg Compound A, second group 20 mg, and third group 80 mg, once daily for 8 weeks. Weekly assessment is administered during the treatment period. The values of the assessment at week 8 are compared to the baseline values with statistical analysis.

Example 3

Human Clinical Trial, RLS Treatment with an $A_{2A}$ Antagonist

In order to assess the efficacy of a representative $A_{2A}$ antagonist in treating RLS, a clinical trial was initiated and conducted in accordance with standard procedures. Briefly, the total score in International RLS Rating Scale (IRLSRS) and total PLMS index (polysomnography; PLMS index represents the number of periodic limb movements per hour of sleep) of the patients were measured to evaluate the efficacy of Compound A in RLS [Understanding and Diagnosing Restless Legs Syndrome (2003), Restless Legs Syndrome Foundation, 819 Second Street, SW Rochester, Minn. 55902].

Scoring for IRLSRS was made according to the following Instructions for Examiner (Maximum IRLSRS total score is 40).

The Examiner was instructed to have the patient rate his/her symptoms for the following ten questions. The patient and not the examiner made the ratings, but the examiner was available to clarify any misunderstandings the patient may have had about the questions. Either the examiner or the patient marked the answers on the form. In questions 1, 2, 4, 5, 6, 9 and 10, the following scoring was used: (4) Very severe; (3) Severe; (2) Moderate; (1) Mild; and (0) None.

1. Overall, how would you rate the RLS discomfort in your legs or arms?

2. Overall, how would you rate the need to move around

3. Overall, how much relief of your RLS arm or leg discomfort do you get from moving around?

(4) No relief
    (3) Slight relief
    (2) Moderate relief
    (1) Either complete or almost complete relief
    (0) No RLS symptoms and therefore question does not apply 4. Overall, how severe is your sleep disturbance from your RLS symptoms?

5. How severe is your tiredness or sleepiness from your RLS symptoms?

6. Overall, how severe is your RLS as a whole?

7. How often do you get RLS symptoms?
    (4) Very severe (This means 6 to 7 days a week.)
    (3) Severe (This means 4 to 5 days a week.)
    (2) Moderate (This means 2 to 3 days a week.)
    (1) Mild (This means 1 day a week or less.)
    (0) None 8. When you have RLS symptoms, how severe are they on an average day?
    (4) Very severe (This means 8 hours per 24 hour day or more.)
    (3) Severe (This means 3 to 8 hours per 24 hour day.)
    (2) Moderate (This means 1 to 3 hours per 24 hour day.)
    (1) Mild (This means less than 1 hour per 24 hour day.)
    (0) None 9. Overall, how severe is the impact of your RLS symptoms on your ability to carry out your daily affairs, for example carrying out a satisfactory family, home, social, school, or work life?

10. How severe is your mood disturbance from your RLS symptoms—for example angry, depressed, sad, anxious, or irritable?

Patients diagnosed with idiopathic RLS were withheld from the medication from the time of screening until the end of treatment. After tapering all RLS medications, patients were screened for eligibility. At Week −2, patients were admitted to the clinic on the night preceding the visit day to be adapted to the sleep environment of the laboratory. After screening, IRLSRS total score and total PLMS index of the patients were measured on Day −1 in order to establish a baseline and to assess the range of RLS fluctuation. Only patients with moderate to severe RLS (15 and more IRLSRS total scores) were enrolled in the study. And patients who showed more than 35% fluctuation in IRLSRS and/or polysomnography between Week −1 visit and Day −1 visit (a base line) were not subjected to further study.

Treatment with Compound A (80 mg, once a day) began on the day following Day −1 visit and continued for the next 6 weeks. The last dose of Compound A was taken on the day of Week 6 visit. At Week 8, patients received RLS assessments (IRLSRS total score and total PLMS index). The inhibition ratio for each score was calculated by the following equation.

Inhibition Ratio(%)={[(Score at Day−1)−(Score at Week 8)]/(Score at Day−1)}×100

The results are shown in Table 1 below.

TABLE 1

|  | Baseline (Day-1) mean (SD) | Week 8 mean (SD) | Inhibition Ratio (%) |
|---|---|---|---|
| IRLSRS Total Score | 32.5 (4.39) | 23 (8.04) | 29.2 |
| Total PLMS Index | 45 (15.41) | 24.67 (23.89) | 45.2 |

N = 4

As shown in Table 1, both IRLSRS total score and total PLMS index decreased at Week 8 from respective baseline values. That is, 80 mg of Compound A once a day for 6 weeks resulted in relief of RLS symptoms and improvement in patients with moderate to severe RLS. These results show for the first time that the adenosine $A_{2a}$ receptor antagonist is effective in the treatment of RLS.

Certain embodiments of the present invention are described in the following examples.

Example 1

Tablets

Tablets having the following composition are prepared in a conventional manner.

Compound A (40 g) is mixed with 286.8 g of lactose and 60 g of potato starch, followed by addition of 120 g of a 10% aqueous solution of hydroxypropyl cellulose. The resultant mixture is kneaded, granulated, and then dried by a conventional method. The granules are refined to give granules used to make tablets. After mixing the granules with 1.2 g of magnesium stearate, the mixture is formed into tablets each containing 20 mg of the active ingredient by using a tablet maker (Model RT-15, Kikusui) having pestles of 8 mm diameter.

The prescription is shown in Table 2.

TABLE 2

| Compound A | 20 mg |
|---|---|
| Lactose | 143.4 mg |
| Potato Starch | 30 mg |
| Hydroxypropyl Cellulose | 6 mg |
| Magnesium Stearate | 0.6 mg |
|  | 200 mg |

Example 2

Capsules

Capsules having the following composition are prepared in a conventional manner.

Compound A (200 g) is mixed with 995 g of Avicel and 5 g of magnesium stearate. The mixture is put in hard capsules No. 4 each having a capacity of 120 mg by using a capsule filler (Model LZ-64, Zanashi) to give capsules each containing 20 mg of the active ingredient.

The prescription is shown in Table 3.

TABLE 3

| Compound A | 20 mg |
|---|---|
| Avicel | 99.5 mg |
| Magnesium Stearate | 0.5 mg |
|  | 120 mg |

Example 3

Injections

Injections having the following composition are prepared in a conventional manner.

Compound A (1 g) is dissolved in 100 g of purified soybean oil, followed by addition of 12 g of purified egg yolk lecithin and 25 g of glycerin for injection. The resultant mixture is made up to 1,000 ml with distilled water for injection, thoroughly mixed, and emulsified by a conventional method. The resultant dispersion is subjected to aseptic filtration by using 0.2 µm disposable membrane filters, and then aseptically put into glass vials in 2 ml portions to give injections containing 2 mg of the active ingredient per vial.

The prescription is shown in Table 4.

TABLE 4

| Compound A | 2 mg |
|---|---|
| Purified Soybean Oil | 200 mg |
| Purified Egg Yolk Lecithin | 24 mg |
| Glycerine for Injection | 50 mg |
| Distilled Water for Injection | 1.72 ml |
|  | 2.00 ml |

The invention claimed is:

1. A method of treating restless legs syndrome, comprising administering an effective amount of at least one adenosine A2A receptor antagonist to a patient suffering from restless legs syndrome, which patient does not have Parkinson's disease, wherein the adenosine A2A receptor antagonist is a xanthine derivative or a pharmaceutically acceptable salt thereof, wherein the xanthine derivative is represented by the following formula (I-A):

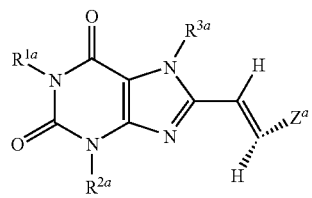

(I-A)

wherein $R^{1a}$ and $R^{2a}$ independently represent methyl or ethyl; $R^{3a}$ represents hydrogen or lower alkyl; and $Z^a$ represents

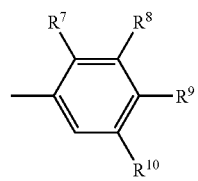

(in which at least one of $R^7$, $R^8$ and $R^9$ represents lower alkyl or lower alkoxy and the others represent hydrogen; and $R^{10}$ represents hydrogen or lower alkyl) or

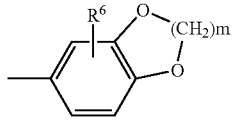

(in which $R^6$ represents hydrogen, hydroxy, lower alkyl, lower alkoxy, halogen, nitro or amino; and m represents an integer of 1 to 3).

2. The method of treating restless legs syndrome according to claim 1, wherein the xanthine derivative is (E)-8-(3,4-dimethoxystyryl)-1,3-diethyl-7-methylxanthine.

3. A method of treating nocturnal myoclonus, comprising administering an effective amount of at least one adenosine A2A receptor antagonist to a patient suffering from nocturnal myoclonus, which patient does not have Parkinson's disease, wherein the adenosine A2A receptor antagonist is a xanthine derivative or a pharmaceutically acceptable salt thereof, wherein the xanthine derivative is represented by the following formula (I-A):

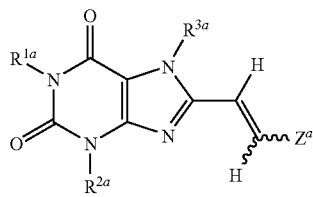

wherein $R^{1a}$ and $R^{2a}$ independently represent methyl or ethyl; $R^{3a}$ represents hydrogen or lower alkyl; and $Z^a$ represents

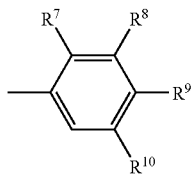

(in which at least one of $R^7$, $R^8$ and $R^9$ represents lower alkyl or lower alkoxy and the others represent hydrogen; and $R^{10}$ represents hydrogen or lower alkyl) or

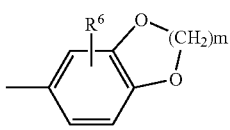

(in which $R^6$ represents hydrogen, hydroxy, lower alkyl, lower alkoxy, halogen, nitro or amino; and m represents an integer of 1 to 3).

4. The method of treating nocturnal myoclonus according to claim 3, wherein the xanthine derivative is (E)-8-(3,4-dimethoxystyryl)-1,3-diethyl-7-methylxanthine.

* * * * *